US00RE35059E

United States Patent [19]

Schmidhauser

[11] E Patent Number: Re. 35,059

[45] Reissued Date of Patent: Oct. 10, 1995

[54] BIS(4-HYDROXYPHENYL)CYCLOALKANES

[75] Inventor: John C. Schmidhauser, Schenectady, N.Y.

[73] Assignee: General Electric Company, Schenectady, N.Y.

[21] Appl. No.: 341,232

[22] Filed: Nov. 17, 1994

Related U.S. Patent Documents

Reissue of:

[64] Patent No.: 5,306,832
Issued: Apr. 26, 1994
Appl. No.: 132,979
Filed: Oct. 7, 1993

U.S. Applications:

[62] Division of Ser. No. 989,316, Dec. 11, 1992, Pat. No. 5,300,622.

[51] Int. Cl.[6] ..... C07D 335/02

[52] U.S. Cl. ..... 549/13

[58] Field of Search ..... 546/226; 549/13

[56] References Cited

U.S. PATENT DOCUMENTS

| | | | |
|---|---|---|---|
| 3,437,637 | 4/1969 | Matzner et al. | 528/196 |
| 3,461,098 | 8/1969 | Cotter et al. | 528/196 |
| 5,013,849 | 5/1991 | Rule | 549/28 |

OTHER PUBLICATIONS

Diederich et al. "New water soluble macrocycles of paracyclophane type" Tetrahedron Lett. 23 3167–3170 (1982).

Diederich et al. "Designed water soluble macrocyclic esterases: from nonproductive to productive binding" J. Org. Chem. 53 2744–2757 (1988).

*Primary Examiner*—Ceila Chang

*Attorney, Agent, or Firm*—William H. Pittman

[57] ABSTRACT

A heterocyclohexylidenebisphenol having the formula

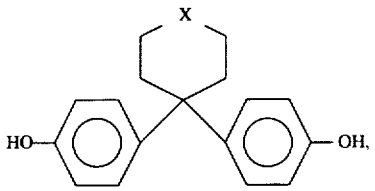

(1)

wherein X is S, SO[,] *or* $SO_2$ [or N—COR and R is a $C_{1-4}$ primary or secondary alkyl or phenyl optionally substituted by an ethyl or 1–2 methyl groups] may be prepared by the reaction of phenol or a similar compound with the corresponding thiopyranone [or piperidone]. The thio compound may be oxidized to the corresponding *sulfoxide or* sulfone. Polycarbonates prepared from said heterocyclic bis(4-hydroxyphenyl) cycloalkanes having high glass transition temperatures and are expected to be ductile.

4 Claims, No Drawings

BIS(4-HYDROXYPHENYL)CYCLOALKANES

Matter enclosed in heavy brackets [ ] appears in the original patent but forms no part of this reissue specification; matter printed in italics indicates the additions made by reissue.

This application is *a re-issue of Ser. No. 08/132,979 filed Oct. 7, 1993, now U.S. Pat. No. 5,306,832, which is* a division[,] of application Ser. No. 07/989,316, filed Dec. 11, 1992, *now U.S. Pat. No. 5,300,622.*

This invention relates to new compositions of matter, and more particularly to new polycarbonates and precursors thereof.

Polycarbonates are a class of high performance engineering resins characterized by optical clarity, high ductility and other advantageous properties. They are frequently employed as lenses and windows by reason of their transparency. Bisphenol A polycarbonate is the principal commercial available resin of this type. It is derived from 2,2-bis(4-hydroxyphenyl)propane, and typically has a glass transition temperature of about 150° C.

It is of increasing interest to prepare polycarbonates which, while retaining the ductility of bisphenol A polycarbonates, have higher glass transition temperatures and are therefore more resistant to softening when heated. Typical areas of application of such polycarbonates are in the preparation of automotive headlamp lenses, which are becoming smaller in size and therefore characterized by closer proximity of the lens to the heat-generating light source, and in windows for aircraft operating at high altitudes, wherein solar heating effects may be pronounced.

The present invention provides a class of polycarbonates which have glass transition temperatures at least 35° C. and up to 84° C. higher than those of bisphenol A polycarbonates, and which are expected to be ductile. Also provided is a series of bisphenols convertible to said polycarbonates.

In one of its aspects, the invention includes heterocyclic bis(4-hydroxyphenyl)cycloalkanes (hereinafter sometimes simply "heterocyclic bisphenols") having the formula (I)

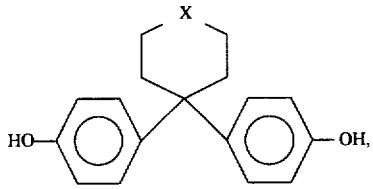

wherein X is S, SO[,] *or* $SO_2$ [or N-OCOR and R is a $C_{1-4}$ primary or secondary alkyl or $C_{6-8}$ aromatic radical].

The X value in the heterocyclic bisphenols of this invention may be sulfur[,] *or a sulfoxide or* sulfone group [or an acylated nitrogen atom. In the latter, R may be an alkyl radical such as methyl, ethyl, 1-propyl, 2-propyl, 1-butyl, 2-butyl or 2-methylpropyl, or an aromatic radical such as phenyl, tolyl or xylyl. Methyl is preferred].

The heterocyclic bisphenols of this invention in which X is sulfur [or acylated nitrogen] may be prepared by the reaction of phenol with tetrahydrothiopyran-4-one [or an acylated 4-piperidone] in the presence of an acidic catalyst. A mercaptan is preferably also present as a reaction promoter. The compounds in which X is sulfur may be converted to those in which X is SO and/or $SO_2$ by oxidation with a suitable oxidizing agent; for example, with a carboxylic peracid such as peracetic acid in acidic medium, typically glacial acetic acid.

The preparation of the heterocyclic bisphenols of this invention is illustrated by the following examples. Molecular structures were determined by proton and carbon-13 nuclear magnetic resonance spectroscopy and mass spectrometry.

EXAMPLE 1

A mixture of 10 grams (86 mmol.) of tetrahydrothiopyran-4-one, 81 grams (860 mmol.) of phenol and 10 grams of a cation exchange resin in the acid form, having a hydrogen ion concentration of 4 milliequivalents per gram and modified with a thiol promoter in the amount of 0.8 milliequivalent per gram, was heated for 4 hours at 75° C. The resulting orange solution was filtered through a glass funnel while hot. Upon cooling, a solid formed and was removed by filtration. The filtrate was mixed with 100 ml. of methylene chloride, whereupon a second crop of solid deposited and was collected by filtration.

The combined crude solids weighed 28.6 grams. They were recrystallized from chlorobenzene to yield the desired 4,4-bis(4hydroxyphenyl)thiopyran as pale tan crystals. The yield was 18.35 grams (75% of theoretical).

EXAMPLE 2

[A mixture of 100 grams (1.06 moles) of phenol and 3 ml. of dodecylthiol was heated under nitrogen to 50° C., and gaseous hydrogen chloride was passed in for 15 minutes. Passage of hydrogen chloride was continued as 15 grams (106 mmol.) of 1-acetyl- 4-piperidone was added over 5 minutes. Hydrogen chloride treatment was continued for 20 minutes, after which the mixture was stirred for 20 hours at 75° C. It was then cooled to room temperature and diluted with ethyl acetate and saturated sodium bicarbonate solution, whereupon the crude product precipitated as a white solid. It was collected by filtration and washed with water until neutral. The crude yield was 25.9 grams (78% of theoretical). A portion of the crude product was recrystallized from glacial acetic acid and was identified as the desired 4,4-bis(4-hydroxyphenyl)-1-acetylpiperidine.

EXAMPLE 3]

A slurry of 5 grams (17 mmol.) of the product of Example 1 in 20 ml. of glacial acetic acid was added over 20 minutes, at ice bath temperature, to 8.86 grams (37.2 mmol.) of a 32% (by weight) solution of peracetic acid in glacial acetic acid. The mixture was allowed to warm to room temperature over 14 hours, whereupon it turned opaque. The precipitated solids were filtered through a glass funnel and washed with two portions of glacial acetic acid. The crude yield of the desired 4,4-bis(4-hydroxyphenyl)pentamethylenesulfone was 4.25 grams (77% of theoretical). The product was recrystallized from methanol and water to yield 3.5 grams (63% of theoretical) of the pure product.

The heterocyclic bisphenols of this invention may be converted to polycarbonates by reaction with a carbonate source such as phosgene or dimethyl carbonate, using conventional techniques. These include melt polymerization, interfacial polymerization and interfacial conversion to bischloroformate followed by polymerization. Chain termination agents such as phenol may also be employed.

Such polycarbonates are another aspect of the invention; they comprise heterocyclohexylidenebisphenol structural units of the formula

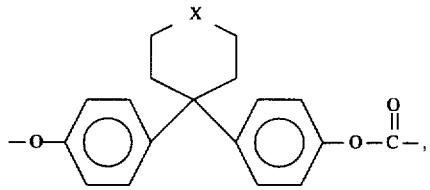

(II)

wherein X is as previously defined.

Polycarbonates of the invention in which X is SO and/or $SO_2$ may also be prepared from corresponding polycarbonates in which X is S by oxidation with a suitable oxidizing agent, typically a peracid.

The polycarbonates of this invention include both homopolycarbonates and copolycarbonates. Copolycarbonates may include more than one molecular species of the heterocyclohexylidenebisphenol structural units. They may also contain units corresponding to the dihydroxy compounds disclosed by name or formula (generic or specific) in U.S. Pat. No. 4,217,438, the disclosure of which is incorporated by reference herein. Such copolycarbonates typically comprise about 25–75% by number of bis(4-hydroxybiphenylyl)alkane units, with the balance being other units.

Said other units include those having the formula $$-O-A^1-Y-A^2-O-\overset{\overset{\displaystyle O}{\|}}{C}-, \qquad \text{(III)}$$

wherein each of $A^1$ and $A^2$ is a monocyclic divalent aromatic radical and Y is a bridging radical in which one or two atoms separate $A^1$ from $A^2$. The free valence bonds in formula III are usually in the meta or para positions of $A^1$ and $A^2$ in relation to Y.

The $A^1$ and $A^2$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gem-alkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred units of formula III are 2,2-bis(4-phenylene)propane carbonate units, which are derived from bisphenol A and in which Y is isopropylidene and $A^1$ and $A^2$ are each p-phenylene.

The preparation of the polycarbonates of this invention is illustrated by the following examples. Molecular weights were determined by gel permeation chromatography relative to polystyrene.

EXAMPLES [4–9] *3–6*

Various bisphenol combinations in the amount of 8.42% w/v were combined with methylene chloride and with the following volume percentages of other materials, all percentages being based on said methylene chloride[,].

Water- 90%;

5% w/v triethylamine solution in methylene chloride-1.5%;

5% w/v phenol solution in methylene chloride-2%.

Phosgene was passed into the mixtures, with stirring, for 10 minutes to a total of 6% w/v, as the pH values of the aqueous phases were maintained between 10 and 11 by the addition of 10% aqueous sodium hydroxide solution. The mixtures were then purged with nitrogen for 15 minutes and the organic phases separated, washed twice with 3% aqueous hydrochloric acid solution and four times with water and dried over magnesium sulfate. The dried solutions were poured into methanol and the precipitated solids were redissolved in methylene chloride, precipitated by the addition of acetonitrile, redissolved again in methylene chloride and reprecipitated by the addition of methanol. The resulting copolycarbonates were dried to constant weight. Their identities and properties are listed in the following table.

| Example | Bisphenol, mole % | Mw | Mw/Mn | Tg, °C. |
|---|---|---|---|---|
| [4]3 | Ex. 1, 100 | 50,000 | 1.91 | 209 |
| [5]4 | Ex. 1, 50<br>Bisphenol A, 50 | 90,500 | 1.68 | 186 |
| [6]5 | Ex. 1, 50<br>Ex. [3]2, 50 | — | — | 234 |
| [7 | Ex. 2, 100 | — | — | 221 |
| 8 | Ex. 2, 50<br>Bisphenol A, 50] | 70,000 | 1.74 | 207 |
| [9]6 | Ex. [3]2, 50<br>Bisphenol A, 50 | 50,800 | 1.57 | 185 |

Similar results were obtained with bisphenol solutions in methylene chloride as dilute as 3.5% w/v and triethylamine, phenol and phosgene proportions as low as 0.75%, 1% and 3%, respectively.

EXAMPLE [10] *7*

A solution of 300 mg. of the polycarbonate of Example [4] *3* and 116 mg. (0.67 mmol.) of m-chloroperbenzoic acid in 50 ml. of methylene chloride was stirred at room temperature for 1 hour, after which the product was isolated by precipitation into methanol, filtration and drying in a vacuum oven. It was the desired heterocyclohexylidenebisphenol sulfoxide/sulfone copolycarbonate, and had a glass transition temperature of 283° C.

What is claimed is:

1. A heterocyclohexylidenebisphenol having the formula

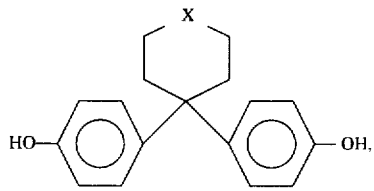

(I)

wherein X is S, SO[,] *or* $SO_2$ [or N—OCOR and R is a $C_{1-4}$ primary or secondary alkyl or $C_{6-8}$ aromatic radical].

2. A heterocyclohexylidenebisphenol according to claim 1 wherein X is S.

3. A heterocyclohexylidenebisphenol according to claim 1 wherein X is SO.

4. A heterocyclohexylidenebisphenol according to claim 1 wherein X is $SO_2$.

[5. A heterocyclohexylidenebisphenol according to claim 1 wherein X is N—OCOR].

[6. A heterocyclohexylidenebisphenol according to claim 5 wherein R is methyl.]

* * * * *